(12) United States Patent
Okun et al.

(10) Patent No.: US 9,610,437 B2
(45) Date of Patent: Apr. 4, 2017

(54) APPARATUSES AND METHODS FOR SECURING DEEP BRAIN STIMULATION LEADS

(71) Applicant: University of Florida Research Foundation, Inc., Gainesville, FL (US)

(72) Inventors: Michael Scott Okun, Gainesville, FL (US); Kelly D. Foote, Gainesville, FL (US); Mark Roger Davidson, Florahome, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 49 days.

(21) Appl. No.: 14/448,095

(22) Filed: Jul. 31, 2014

(65) Prior Publication Data

US 2015/0039063 A1 Feb. 5, 2015

Related U.S. Application Data

(60) Provisional application No. 61/861,022, filed on Aug. 1, 2013.

(51) Int. Cl.
*A61N 1/05* (2006.01)
(52) U.S. Cl.
CPC ......... *A61N 1/0539* (2013.01); *A61N 1/0534* (2013.01)
(58) Field of Classification Search
CPC .. A61N 1/0526; A61N 1/0529; A61N 1/0531; A61N 1/0534; A61N 1/0539
USPC ............................................. 607/45, 116, 117
See application file for complete search history.

(56) References Cited

U.S. PATENT DOCUMENTS

| 5,927,277 | A | * | 7/1999 | Baudino | ............... | A61N 1/0539 600/386 |
| 7,988,674 | B2 | | 8/2011 | Adams et al. | | |
| 2005/0182420 | A1 | * | 8/2005 | Schulte | ................ | A61N 1/0539 606/130 |
| 2006/0129203 | A1 | * | 6/2006 | Garabedian | .......... | A61N 1/0531 607/45 |
| 2008/0103578 | A1 | * | 5/2008 | Gerber | ................ | A61N 1/0539 607/149 |
| 2009/0112327 | A1 | * | 4/2009 | Lane | .................... | A61N 1/0539 623/17.19 |
| 2009/0118804 | A1 | * | 5/2009 | Moffitt | ................ | A61B 5/6864 607/116 |

(Continued)

*Primary Examiner* — Allen Porter, Jr.
(74) *Attorney, Agent, or Firm* — Thomas | Horstemeyer LLP; Christopher B. Linder; Randy R. Schoen

(57) ABSTRACT

Various examples are provided for securing deep brain stimulation (DBS) leads. In one example, among others, a DBS cap for securing a DBS lead includes a base ring adapted to be mounted within a counterbore opening formed in the skull, a lead securing element that mounts to the base ring, and, a top cover that mounts to the base ring. In another example, a method for securing a DBS lead includes forming a counterbore opening in the skull, securing a DBS cap within the counterbore opening, passing a DBS lead through the DBS cap and the counterbore opening and positioning a tip of the lead in brain tissue, and securing the DBS lead to the DBS cap using an adhesive. The skull opening includes a lower bore, a concentric upper bore, and a step positioned at the interface of the upper and lower bores.

22 Claims, 5 Drawing Sheets

(56) References Cited

U.S. PATENT DOCUMENTS

| | | | | |
|---|---|---|---|---|
| 2012/0143297 A1* | 6/2012 | Greene | ............... | A61N 1/0539 607/116 |
| 2012/0316628 A1* | 12/2012 | Lopez | .................. | A61N 1/0539 607/116 |
| 2013/0066410 A1* | 3/2013 | Funderburk | ......... | A61N 1/0539 607/116 |
| 2014/0073859 A1* | 3/2014 | Schorn | ............... | A61B 17/3468 600/300 |

* cited by examiner

APPARATUSES AND METHODS FOR SECURING DEEP BRAIN STIMULATION LEADS

CROSS REFERENCE TO RELATED APPLICATIONS

This application claims priority to co-pending U.S. provisional application entitled "APPARATUSES AND METHODS FOR SECURING DEEP BRAIN STIMULATION LEADS" having Ser. No. 61/861,022, filed Aug. 1, 2013, the entirety of which is hereby incorporated by reference.

BACKGROUND

Deep brain stimulation (DBS) is a surgical treatment involving the implantation of a pulse generator that sends therapeutic electrical impulses to specific parts of the brain. DBS in precisely selected brain locations can provide therapeutic benefit for otherwise treatment-resistant movement and affective disorders, such as Parkinson's disease, tremor, dystonia and obsessive-compulsive disorder.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

Figure 1:
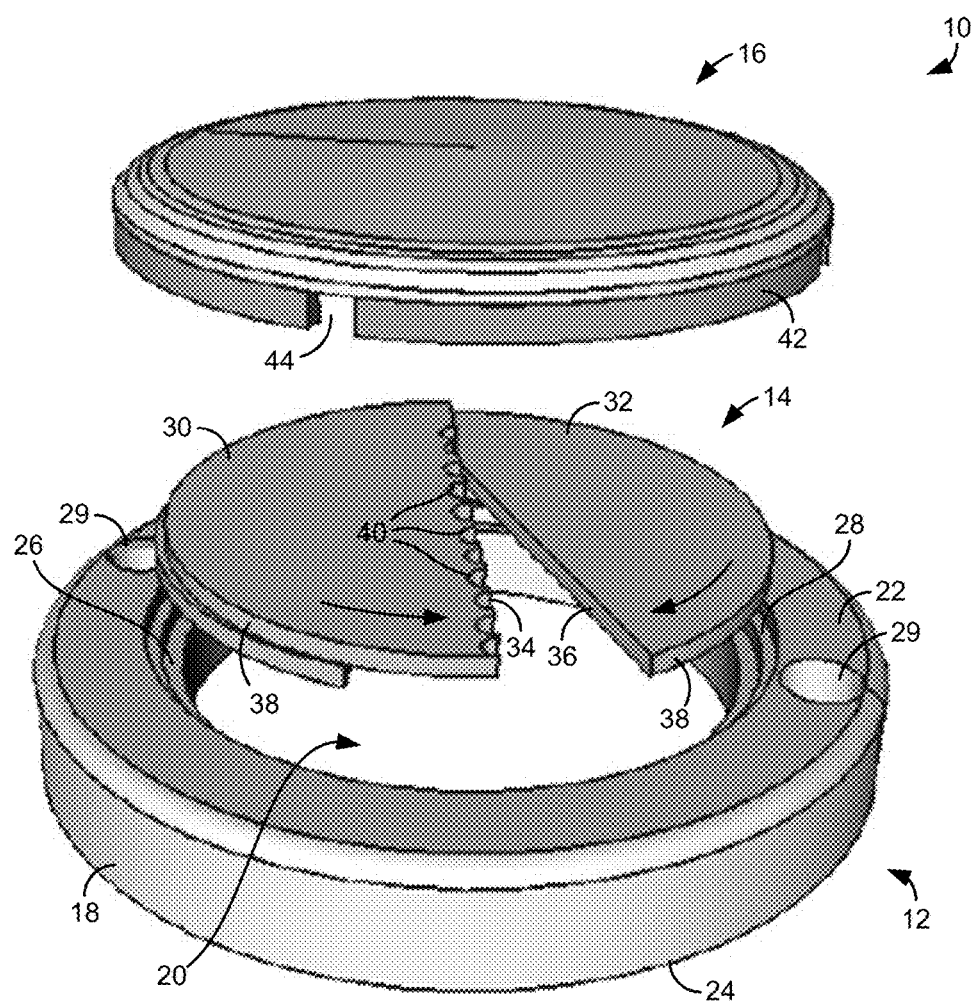
FIG. 1 is an exploded perspective view of an embodiment of a deep brain stimulation (DBS) cap adapted to secure a DBS lead relative to the skull in accordance with various embodiments of the present disclosure.

The typical DBS system comprises the pulse generator, which is typically implanted within the patient's chest or abdominal wall (e.g., under the skin below the clavicle), a DBS lead that is implanted in the brain through an burr hole in the skull, and a connection cable (sometimes referred to as the "extension") that is tunneled under the skin to connect the DBS lead to the pulse generator. The DBS lead typically comprises a series of elongated conductive wires surrounded by polymer insulation. The polymer-encased wires are connected at each end of the lead to a series of exposed electrodes. The electrodes at the distal end of the lead are implanted in contact with desired regions of the brain to deliver the therapeutic electrical impulses. In the typical case, the tip of the lead is positioned in a region deep within the brain. In order to obtain the desired outcome from the system, it is critical that the lead tip is positioned at a precise location within the brain both during the surgical procedure and thereafter.

A DBS cap is typically attached to the skull at the burr hole site and used to secure the DBS lead to the skull at the entry site to ensure that the intracranial lead does not migrate and the positions of the therapeutic contacts remain constant in the brain. While such caps normally incorporate locking elements that are intended to prevent movement of the lead, the locking elements often fail to prevent migration of the lead either intra-operatively while the lead is being secured, or post-operatively due to some inward or outward axial force. If significant migration of the intracranial electrodes occurs, the beneficial therapeutic effect of DBS can be lost, resulting in the need for reprogramming of the device, or even further surgical intervention to replace the displaced DBS lead.

In addition to their poor performance at preventing DBS lead migration, existing DBS cap designs protrude from the outer surface of the skull. This cap protrusion produces a poor cosmetic result and predisposes patients to the development of delayed scalp erosions with exposure and bacterial contamination of implanted DBS hardware. This serious, delayed complication of DBS surgery requires surgical intervention to repair the scalp erosion and, when purulent or life threatening infections result, may require removal of the DBS hardware—with loss of therapeutic benefit—in order to eradicate the infection. The relatively common occurrence of scalp erosion at the site of a protruding DBS cap warrants the development of a DBS cap that can be readily installed flush with the outer surface of the skull to eliminate cap protrusion and minimize the risk for development of this serious complication.

As described above, it would be desirable to have a more effective apparatus and method for securing a deep brain stimulation (DBS) lead that ensures that the lead and its therapeutic contacts in the brain do not migrate. Disclosed herein are examples of such apparatuses and methods. In one embodiment, an apparatus comprises a DBS cap that mounts to the skull under the scalp and secures a DBS lead with a securing element that incorporates an adhesive that prevents the lead from moving relative to the cap and, therefore, the skull. In further embodiments, the DBS cap sits within a counterbore opening formed in the skull and is substantially flush with the outer surface of the skull so as to provide an improved aesthetic result and to mitigate delayed scalp irritation and erosion.

In the following disclosure, various specific embodiments are described. It is to be understood that those embodiments are example implementations of the disclosed inventions and that alternative embodiments are possible. All such embodiments are intended to fall within the scope of this disclosure.

FIG. 1 illustrates an embodiment of a DBS cap 10. As shown in the figure, the cap 10 generally comprises a base ring 12, a lead securing element 14, and a top cover 16. Each of these components can be made of a suitable biocompatible material. In some embodiments, the components are made of a metal material, such as stainless steel or titanium, or a polymeric material, such as polycarbonate, polyurethane, polydimethylsiloxane, or a similar biocompatible polymer.

Irrespective of the material used to fabricate the base ring 12, the base ring is generally ring-shaped. Accordingly, the base ring 12 is generally circular, i.e., has a generally circular outer periphery 18, and includes an inner opening 20 that extends from a top surface 22 of the ring to a bottom surface 24 of the ring. Notably, the base ring 12 is devoid of any tabs or wings that extend outward from its generally circular outer periphery 18. The base ring 12 is sized so as to fit within a counterbore opening formed in the skull of the patient. In various implementations, the counterbore opening can be countersunk. In some embodiments, the base ring 12 has an outer diameter of approximately 20 to 30 mm and a height dimension (i.e., the distance between the top and bottom surfaces 22, 24) of approximately 2 to 6 mm. The dimensions of the inner opening 20 can be varied as desired but normally are large enough to facilitate implantation of the DBS lead within the brain tissue and, therefore, large enough to accommodate any apparatus (e.g., guides) used for that purpose. In some embodiments, the inner opening 20 has a diameter of approximately 12 to 16 mm.

As is also shown in FIG. 1, the base ring 12 includes concentric circular grooves or depressions that are located at the interface between the inner opening 20 and the top surface 22 of the ring. In some embodiments, these depressions include a first, lower or inner depression 26 that is adapted to receive the lead securing element 14 and a second, upper or outer depression 28 that is adapted to receive the top cover 16. As is apparent from FIG. 1, the inner (or lower) depression 26 is smaller than the outer (or upper) depression 28. In some embodiments, the inner depression 26 is approximately 14 to 16 mm in diameter and the outer depression 28 is approximately 14 to 18 mm in diameter. In some embodiments the inner depression 26 or outer depression 28 or both may include protrusions or fittings which provide a friction or snap fit of the mating part.

The base ring 12 further comprises mounting holes 29 that are adapted to receive fasteners, such as bone screws, for the purpose of affixing the base ring within a counterbore opening formed in the skull. The mounting holes 29 extend from the top surface 22 of the ring to its bottom surface 24. In some embodiments, two such mounting holes 29 can be provided. In some embodiments, such mounting holes 29 include protrusions or fittings to retain the screws during fastening.

With further reference to FIG. 1, the lead securing element 14 generally includes two opposed pivotable or otherwise translatable members 30 and 32 that are adapted to close like a pair of jaws to clamp inner edges 34 and 36 onto a DBS lead that extends through the inner opening 20 and into the brain. As indicated in the figure, the lead securing element 14 is also generally circular and therefore comprises a generally circular outer periphery 38, which, in some embodiments, is defined by both members 30, 32 of the element. When the two members 30, 32 are pivoted toward each other in the directions identified by the arrows in FIG. 1 to clamp a DBS lead, the outer periphery 38 of the lead securing element 14 can fit within the inner depression 26 of the base ring 12. As is further illustrated in FIG. 1, one of the members (member 30 in this example) can be provided with multiple indentations 40 along its inner edge 34 in which the DBS lead can be positioned. In some embodiments, the indentations 40 are curved and have a radius of curvature that is slightly smaller than the radius of the DBS lead so as to pinch the polymer sheath of the lead to more securely hold it in place in such a way that the internal wires are not crushed or otherwise damaged. In some embodiments, the radius of curvature of the indentations 40 is approximately 0.5 to 2 mm.

While the lead securing element 14 is designed to secure the DBS lead in place, migration, such as pull out, can still occur due to the relatively slippery nature of the polymer sheath of the DBS lead. To prevent such migration, one or both of the inner edges 34, 36 of the element members 30, 32 can be provided with a layer of adhesive that can more securely hold the DBS lead. In some embodiments, the adhesive is a light-curable adhesive that cures when exposed to light within a particular wavelength band, e.g., the ultraviolet (UV) light wavelength band. Moisture-curable and/or air-curable adhesives can also be used as the adhesive. In some embodiments, the adhesive can be covered with a protective membrane (e.g., a protective polymeric membrane) that is removed prior to closing of the members 30, 32. It is noted that further adhesive can be provided on the outer periphery 38 of the lead securing element 14 and/or the inner depression 26 of the base ring 12 to secure the lead securing element to the base ring.

The top cover 16 is adapted to cover the inner opening 20 of the base ring 12 and, therefore, the opening formed through the patient's skull. As shown in FIG. 1, the top cover 16 can be generally circular and therefore have a circular outer periphery 42. Once the DBS lead has been positioned as desired and secured by the securing element (e.g., by curing the adhesive provided thereon), the top cover 16 can be positioned within the outer depression 28 of the base ring 12. In some embodiments, the outer periphery 42 of the top cover 16 and/or the outer depression 28 of the base ring 12 can also be provided with an adhesive that secures the cover in place on the base ring. As is illustrated in FIG. 1, the outer periphery 42 of the top cover 16 can include one or more notches 44 in which the DBS lead can be positioned so as to avoid crimping the lead as it exits the DBS cap 10.

Figure 2A:
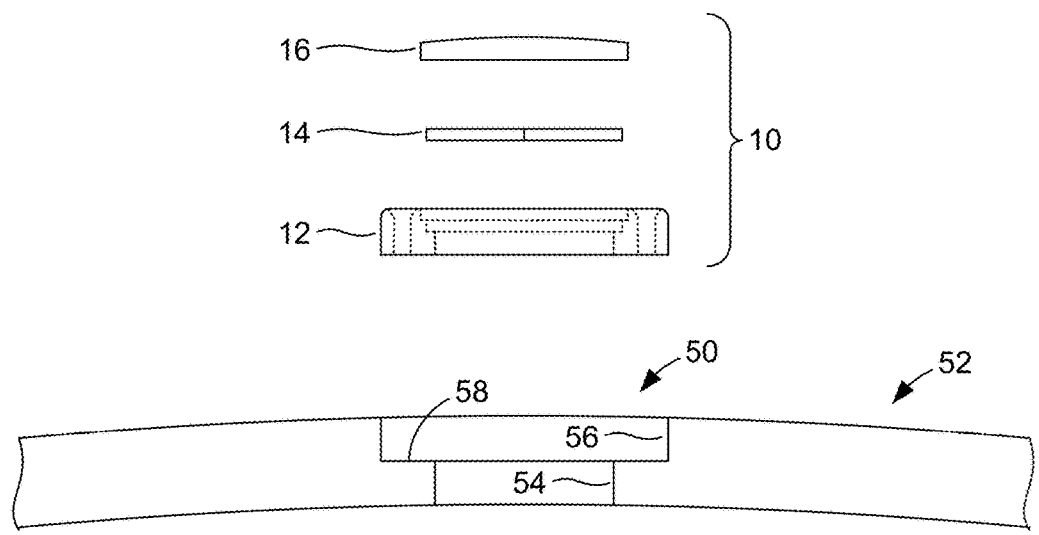
FIGS. 2A and 2B are schematic views of a patient's skull during implantation of a DBS lead and DBS cap, such as the cap shown in FIG. 1 in accordance with various embodiments of the present disclosure.
Figure 2B:
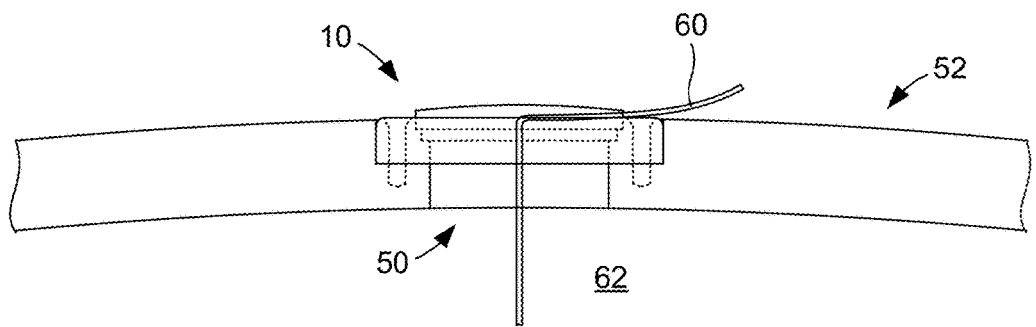

To implant a DBS lead, a counterbore opening is formed through the skull, such as the opening 50 illustrated in FIG. 2A. As is apparent from that figure, the opening 50 extends through the skull 52 and includes a lower bore 54 having a relatively small diameter and a concentric upper bore 56 having a relatively larger diameter. In some embodiments, the opening 50 can be formed using a sterile counterbore drill bit. In some embodiments, the depth of the counterbore is limited by a collar or other indicator on the bit. Forming such an opening 50 creates a step 58 at the interface of the two bores 54, 56 that can support the base ring 12. Once the opening 50 has been formed, the base ring 12 can be inserted into the opening and secured in place with fasteners, such as screws. At this point, the DBS lead can be implanted into the brain through the inner opening 20 (see FIG. 1) of the base ring 12 and through the opening 50 in the skull 52. Once the tip of the DBS lead has been positioned as desired, the lead can be secured in place with the lead securing element 14 and its adhesive, and the top cover 16 can be connected to the base ring 12. FIG. 2B illustrates an example result showing the DBS cap 10 in place within the opening 50 and a DBS lead 60 extending into the brain tissue 62 and out through the DBS cap.

There are several procedure-related and hardware-related complications that may occur as a result of DBS therapy. One such complication is lead migration. Lead migration has been defined as unintended movement of the DBS lead following the securing of the lead to the skull with a capping device or other methodology. There are several potential causes of DBS lead migration including failure of the clamping mechanism, motion of the brain, movement of the cranium, trauma to the skull, and iatrogenic issues (e.g. the lead is accidentally tugged on during pulse generator implantation).

To study the dynamic stability of DBS leads, a model system was used to measure real-time acceleration and displacement of a laboratory based artificial brain and skull that was fitted with an implanted DBS lead. Impact testing recorded the lead position, accelerations of the brain and skull in three axes, and real-time measurements of the impact force. In addition, the tensile strength of the lead clamping was also collected to estimate the force required to displace the DBS lead when a DBS cap was utilized.

Figure 3:
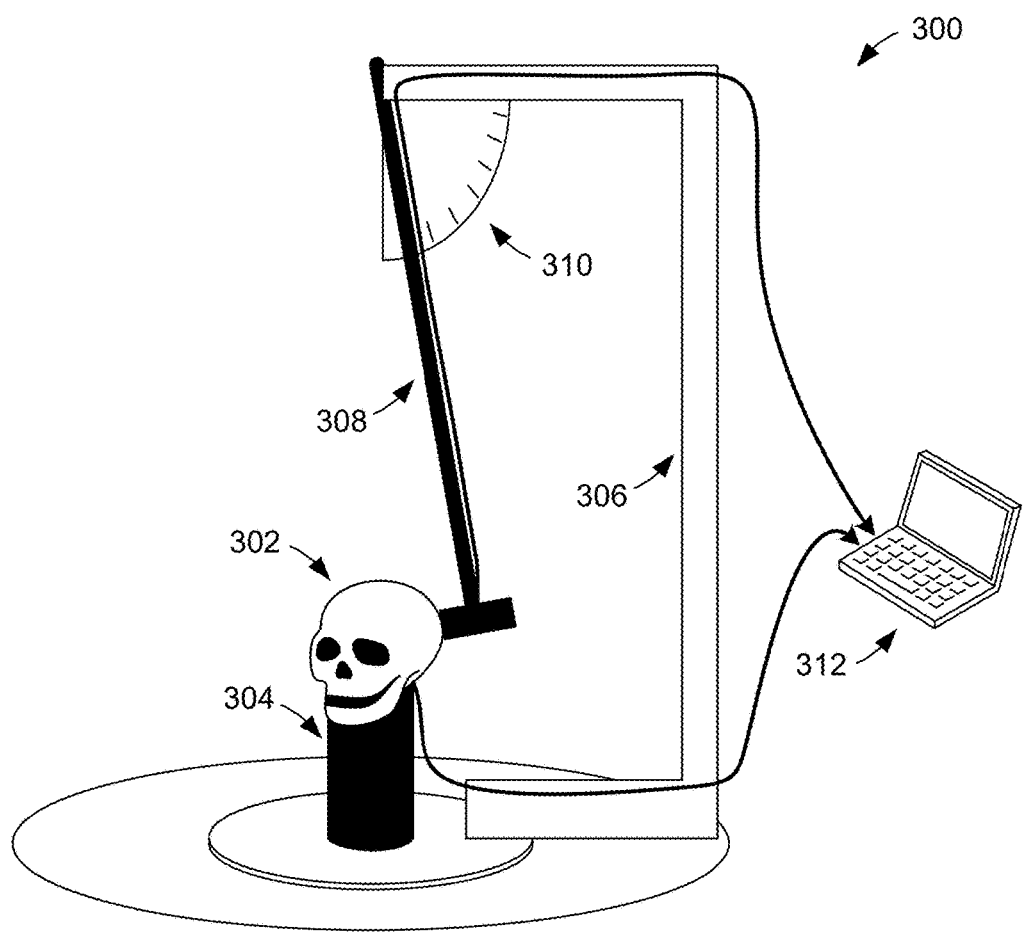
FIG. 3 is a graphical diagram illustrating a test system for evaluation of the DBS cap of FIGS. 1, 2A and 2B in accordance with various embodiments of the present disclosure.

Referring to FIG. 3, shown is an example of a test system 300 used to test the stability of the DBS leads. All testing was performed using the custom-built platform, which was designed to rotate around a PVC molded skull 302 mounted on a molded silicone pedestal 304 to simulate a semirigid neck. The pedestal was attached to a base and the neck stiffness was modified by varying the length of a PVC stiffener. The test system includes a support frame 306 supporting an impact arm 308 with a weight attached to the distal end. A protractor 310 can be used to provide a repeatable release height from which the impact arm 308 can be swung. The impact force was adjusted by increasing or decreasing the angle of the impact arm 308 prior to releasing it. The length of the impact arm 308 may also be adjusted to reach different regions on the skull 302. The skull 302 can be mounted horizontally on the pedestal 304 to measured blows from all directions.

The brain inside the skull 302 was molded using 0.9% agarose gel (Acros Organics) with 0.9% sodium chloride to facilitate proper electrical conductivity. The 0.9% agarose gel was chosen based upon a similar texture and consistency to brain tissue. A mold was created using standard silicone compounds from the model brain t was designed to mate to the skull. After insertion of the molded agarose brain, the cavity was sealed and filled with saline which was used to simulate cerebrospinal fluid.

The model skull 302 was modified to include a standard burr hole for the DBS lead. The burr hole was placed distal to the midline (about 3 cm) and posterior to the coronal suture (about 1 cm). The impact system included an impact arm 308 that was 80 cm in length and a protractor that was a sensor. This protractor 310 was used to measure repeated strikes to the artificial brain. The height of the impact point could be adjusted to provide the desired impact point on the model skull. A layer of polymer clay approximately 1 cm thick was placed on the surface of the impact point to approximate the reduction in impulse that might be expected in the human.

The impact force was measured using an Omega DLC101 force sensor that was threaded onto the weight attached to the distal end of the impact arm 308. This assembly formed the impact surface used to strike the model skull 302. The load cell can measure the impact force. Acceleration of the brain and skull were measured independently through the use of two Omega model ACC-301 three-axis accelerometers. One 3-axis accelerometer was rigidly attached to the top of the skull, and the other 3-axis accelerometer was suspended (during casting) in the agarose brain.

The DBS lead position was measured using a system based on monitoring capacitance changes between the lead, and a large flat plate molded into the gelatin near the electrode position at the base of the model brain. The electrode position was monitored in real time using a custom-built phase-sensitive circuit that measured the phase shift caused by capacitance changes resulting from the motion between the electrodes. This method provided excellent sensitivity for small movements (i.e. sub millimeter movements) while providing improved signal-to-noise ratios through the use of a frequency sensitive lock-in signal detection system.

Each of the 3-axis acceleration signals from both the skull and brain, as well as the DBS lead position and impact force signals were all sampled using a Measurement Computing USB-1608 FS. The signals can be provided to a computing device 312 through wired and/or wireless connections, where the values can be collected and later analyzed using, e.g., custom Matlab® software. An electronic trigger sensed the position of the impact arm 308 just prior to impact with the skull 302. This trigger synchronized data collection with the dynamic force and acceleration so that the maximum meaningful data could be collected for a given time and a particular buffer. Acceleration data was processed by Fourier filtering and integration of the acceleration data to provide time-dependent force and position. The test system 300 generated force and position data for both the brain and the skull. The data was graphically represented as being relative to the measured dynamic impact force. Rotational accelerations were not examined, and were minimized by examining impacts that occurred radial to the axis of the skull 302.

Impact testing was performed by drawing the impact arm 308 back to the desired position, followed by release of the impact arm 308. In each trial, impact data was obtained for a series of impact events with increasing impact force. Each subsequent impact was obtained by increasing the angle of the impact arm 308 by one degree for each impact event. During each impact event, total axial lead motion relative to the reference point in the gelatin brain was recorded. Also recorded was the impact force and acceleration with respect to time. The limit of detection for the axial lead motion was approximately 0.3 mm. The peak impact force measured for the impact when the DBS lead first moved was designated as the threshold force. For those trials where motion was noted, testing was continued by increasing impact force until the applied force was twice the threshold force (if present).

DBS lead movement was recorded based upon capacitance change with distance. The distance of the electrical DBS lead from a reference plate embedded in the cast gelatin brain affects the electrical impedance of the phase-sensitive circuit formed by the plate and the implanted electrode. The impedance change was dominated by the change in capacitance resulting from movement of the electrode with respect to the reference plate. The distance between the electrode and reference plate was proportional to the phase shift between an AC voltage applied between the DBS lead and the plate, and the resulting current flow. The phase variations can be measured using a lock-in amplifier that monitors the current relative to the applied voltage.

The measurement of the distance moved was calibrated using a similar gelatin cast placed in a beaker from the same batch as each of the original gelatin molds. The DBS lead was carefully moved through a series of known distances, and measurements taken, to provide a calibration curve that related the distance to a phase signal obtained by the lock-in detection. The use of an AC signal along with the lock-in detection provided immunity to noise. The estimated maximum error in conversion from voltage to distance was approximately ±0.5 mm. Relative motion was detectable at approximately 0.3 mm. The motion of the electrode could be reliably detected down to less than 0.3 mm.

While the lock-in detection provided excellent sensitivity and noise rejection, it imposed a limitation on time resolution. The lock-in amplifier used to detect phase shifts imposed a measurement time constant on the order of about 300 msec. The motion of the brain relative to the skull 302 was measured using a scale of 10's of milliseconds. Thus, while the motion of the DBS lead could not be followed on the same time scale as the other monitored information, the total movement was measured by the difference in output from the start to finish of the impact measurement. Thus, the net motion for each impact was reported.

In addition, the effect of tissue on the impact was considered as a potential source of error. The tissue effect was modeled by adding 1 cm of polymer clay to the impact surface. The accelerations involved were modeled to be similar to those found in small traumatic impacts such as, e.g., a bump to a head.

Tensile testing of the DBS lead was performed using the same model load cell used for impact measurements, but reconfigured for tensile measurement. The DBS lead was attached to the load cell with a coupling that allowed free off-axis motion (or swiveling) to minimize the effect of any non-axial motion. As the lead was pulled, the tensile force was increased over time. At the point where the lead pulled free of the lead securing element 14 (FIG. 1), the force decreased. This was due to the starting friction of the lead securing element 14 being set higher than the slipping friction. The tensile force applied at the moment of failure was recorded as the holding force of the lead securing element 14.

The DBS leads were secured in a DBS cap 10 (FIG. 1) in the same fashion as they would have been for clinical use in humans. The DBS cap 10 was utilized including the base ring 12, the lead securing element 14, and the top cover 16 of FIG. 1. As the DBS lead passed through the lead securing element 14, it was routed perpendicular to the clamping surface as illustrated in FIG. 2B, so as to maximize the holding force.

For each trial, the tensile holding force was measured both with and without a DBS cap 10 present. In this manner, the holding force of the lead securing element 14 could be distinguished from the holding force that resulted from friction between the gelatin and the DBS lead.

Figure 4A:
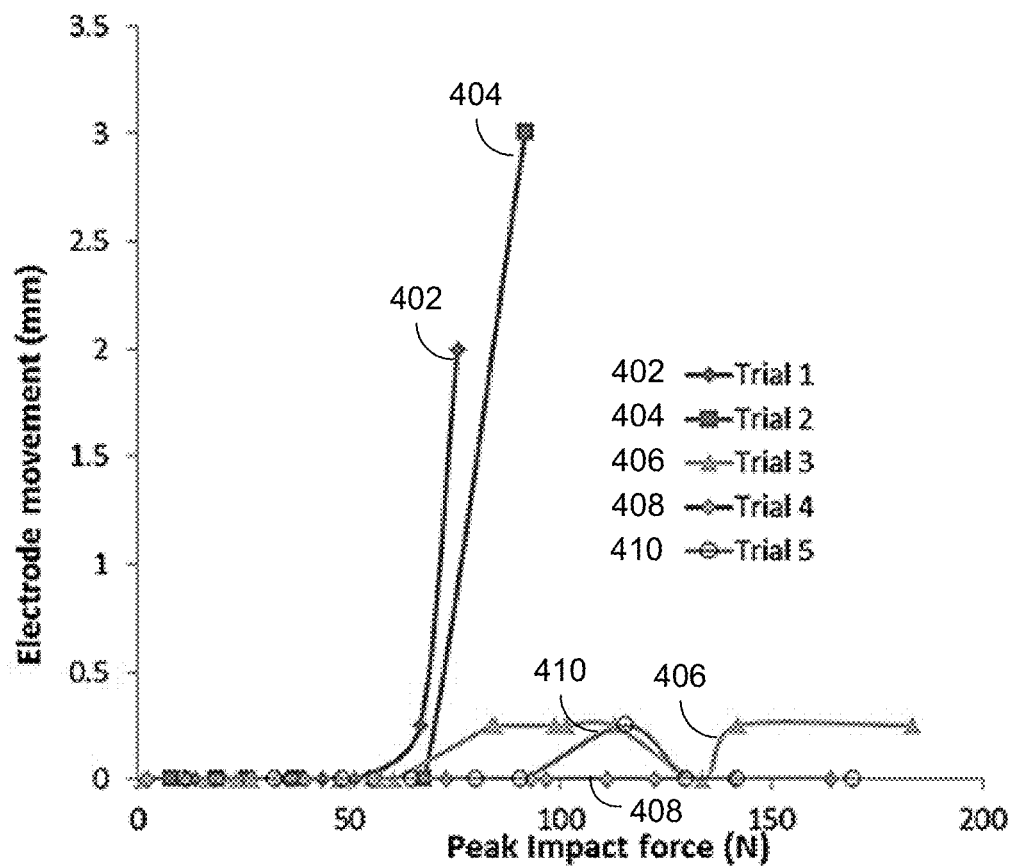
FIGS. 4A through 4D are plots illustrating examples of test data obtained for samples of conventional DBS caps utilizing the test system of FIG. 3 in accordance with various embodiments of the present disclosure.

Only one angle of impact relative to the skull 302 (FIG. 3) was performed. The impact testing was applied to a single location on the same side of the skull 302 as the DBS lead. FIG. 4A shows the motion of the electrode of the DBS lead versus the peak impact force for 5 trials. The first two trials (402 and 404) revealed a large motion (2-3 mm) after 60N of peak impact force. The following 3 trials (406, 408 and 410) demonstrated less than 0.5 mm of movement even at the maximum available impact force of approximately 170 N (about 38 lbs-force). Note that the plotted lines between measurement points are present to help distinguish the measured data. Interestingly, although there was not large scale motion, there were small movement (about 0.3 mm) in 2 of those 3 trials 406 and 410). This small movement tended to be reversed on subsequent impacts. During these three trials (406, 408 and 410), it was noted that the DBS lead had been installed in such a way that it was "bent" between the lead securing element 14 (FIGS. 1, 2A and 2B) and the brain. This may have been due to a kink in the DBS lead or to poor technique during installation, such as moving the DBS lead during fastening of the lead securing element 14.

Figure 4B:
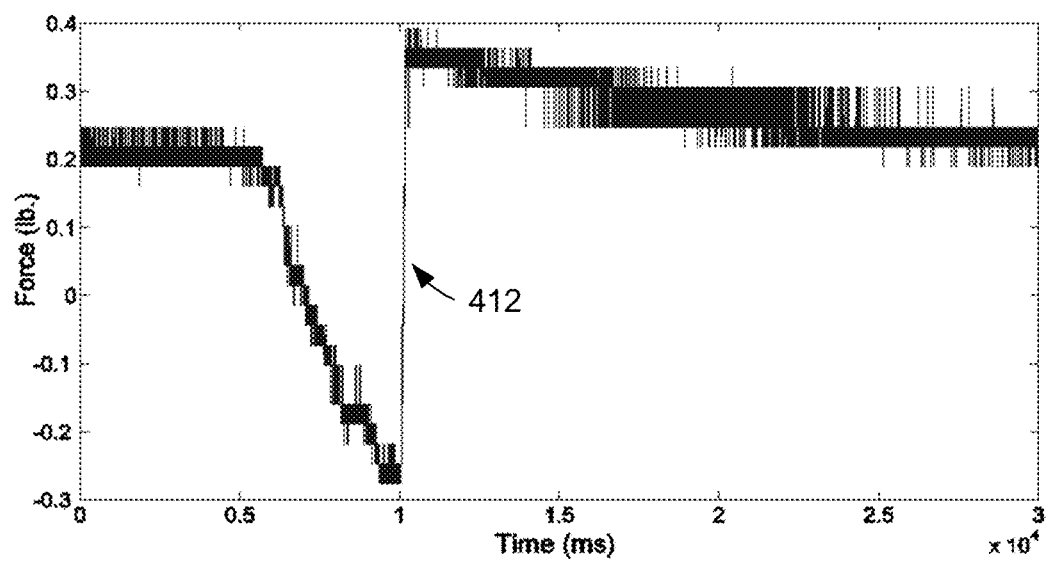
Figure 4C:
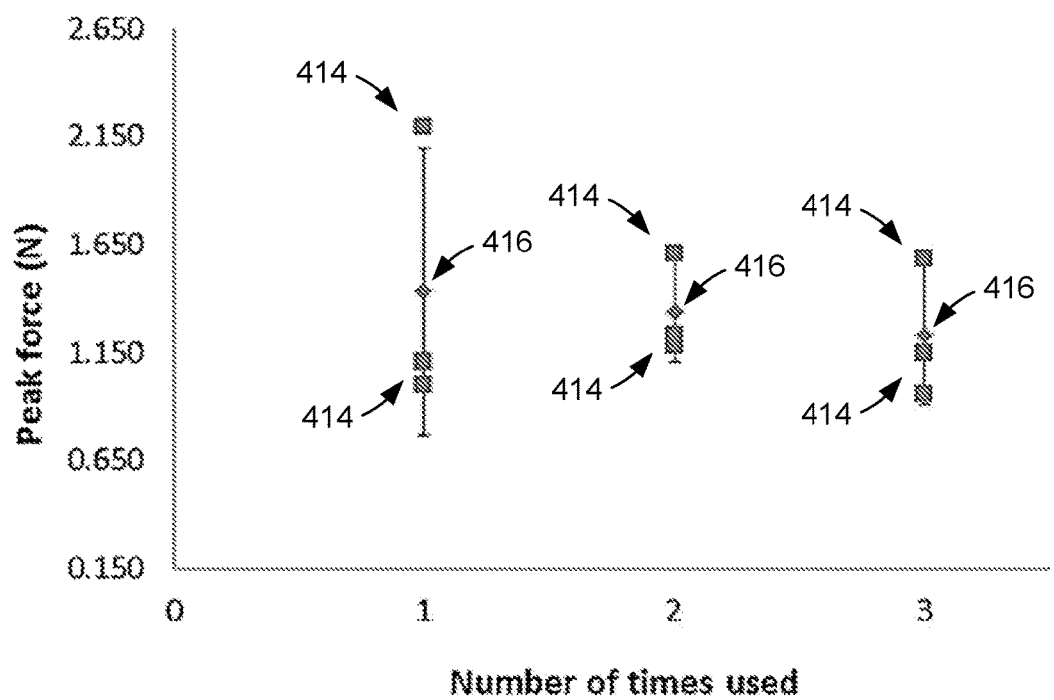

Tensile tests were performed using three separate DBS caps 10 (FIG. 1). Each DBS cap 10 was tested three times to simulate opening and closing of the lead securing element 14 (FIG. 1) during adjustment. This was done purposely as this may occur in clinical DBS applications. FIG. 4B is a plot illustrating raw data of force as a function of time for a sample trial with the DBS cap 10. Positive values represent a compressive force, while negative values represent tension. Note that the tensile force is drastically reduced (412) when the DBS lead slips out of place. Since this is a tensile test, a negative deviation indicates a greater pulling force. The example of FIG. 4B illustrates that at time 1 millisecond, the lead displaced with a tensile force of slightly less that 1.35 N (0.3 lbs-force). The complete results are summarized in FIG. 4C, with the peak force plotted against the first, second, and third "re-closures" (number of times used) of the lead securing element 14. Square-shaped points (414) in FIG. 4C are individual data points for the tests, diamond-shaped points (416) are the mean results for the three DBS caps 10, and the bars indicate the single standard deviation. There was variability observed across the trials, however, less than 2 N of force (0.5 lbs-force) was consistently required to result in lead movement (tensile holding strength).

Figure 4D:
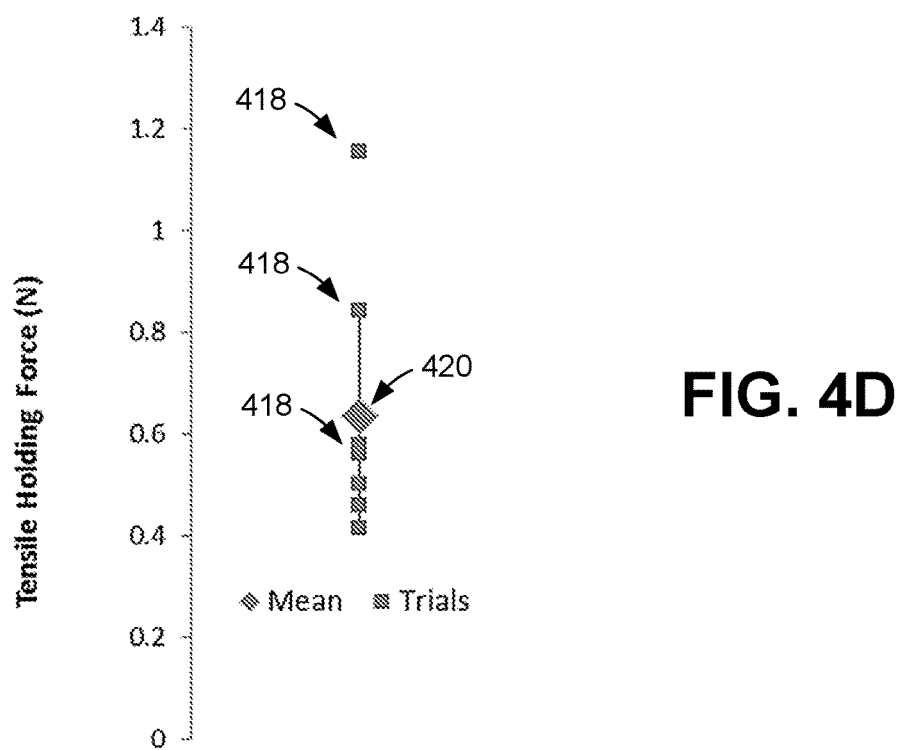

Tensile testing using only the DBS lead implanted in the gelatin brain (without any lead securing element 14 at the skull 302) was also performed. FIG. 4D shows the peak tensile force observed when pulling the DBS lead out of the gel brain 302 (FIG. 3). Square-shaped points (418) represent individual data points from 10 trials. The diamond-shaped point (420) represents the mean with the error bar showing a standard deviation. As shown in FIG. 4D, the mean tensile holding force without the clamp was 0.58 N (0.13 lbs-force).

The impact data obtained using the test system 300 of FIG. 3 reveal that the clamp was a robust solution for moderate head impacts. Interestingly, the DBS leads were more stable in the tests when a small bend was inadvertently introduced. It is unlikely that this would be the case clinically. In the laboratory simulation, the DBS leads were placed by hand, without the benefit of fixturing. That is, no halo fixture was attached to the skull during DBS lead placement. The stylus with the DBS lead was inserted by hand without being guided by the typical mechanical guidance used for surgical cases. Thus any inadvertent non-axial motion, particularly between placing the electrode and clamping, may have led to a small "bend" in the electrode wire such that it was clamped at a point slightly non-axial to the lead. While a stylus is typically used, this part of the assembly had to be removed prior to clamping in the laboratory. The tested system was therefore less rigid.

The results revealed less electrode motion when the DBS lead had some slack. This finding may be better understood when considering the motion of the brain and skull after impact. Following impact, the relative motion between the brain and skull 302 (FIG. 3) was up to 5 mm. The relative motion between the brain and the skull 302, where the DBS lead was fixed, could lead to a "pulling" of the DBS lead away from its initial position. Geometrically, this would result in a curve in the lead. A bend in the lead between the brain and skull may be desirable; however it is unlikely that this could be accomplished during surgery, given the efforts to carefully and accurately place a DBS lead.

The results also revealed that lead motion in the model system did not translate to similar observations in the human clinical setting. Specifically, careful examination of follow-up scans revealed that lead displacement in the human series was associated with little (or no) lead curvature. This suggests the possibility that many of the displacements uncovered by the model system may have been clinically insignificant.

The tensile holding capability of the DBS cap 10 (FIG. 1) was also found to be small. The holding force for tensile "tugging" on the DBS lead was approximately 2 N with approximately 0.6 N derived from friction between the brain and the DBS lead. This force is small enough that even inadvertent "tugs" on the DBS lead during surgery could result in axial displacement. It is also likely that in vivo friction between the brain and the DBS lead is different in the human as compared to the model system, and that the human brain may form a stronger bond than gelatin.

Occasionally, a neurosurgeon may open and repeat closure of a lead securing element 14 (FIG. 1) in the DBS cap 10, especially if DBS lead repositioning is needed. The effectiveness of the repeat closure of the lead securing element 14 by testing the tensile securing ability of the same lead securing element 14 over three trials was examined. The mean holding strength steadily decreased following each of the trials, with a mean reduction of about 14% per trial. Although the holding strength decreased, there was a noted scattering in the data from clamp to clamp, rendering the results difficult to interpret. Interestingly, while clinically neurosurgeons have suggested that repeated clamp use results in reduced effectiveness, in some of trials, the effectiveness actually improved after repeated use.

The DBS cap 10 can be easily used, can be re-usable if repositioning DBS leads is needed, and can be successfully utilized in clinical practice. In addition, it can overcome the issues of poor tensile holding power demonstrated in the measurements. By adding a layer of adhesive, the holding strength can be increased, limited only by the type and application method of the adhesive. An additional advantage is that the embodiments disclosed can result in a cap that is substantially flush with the surface of the skull, resulting in better cosmetic appearance and markedly reducing the likelihood of scalp erosions.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

The invention claimed is:

1. A deep brain stimulation (DBS) cap for securing a DBS lead, the cap comprising:
    a base ring adapted to be mounted within a counterbore opening having concentric lower and upper bores formed in a skull, the upper bore larger in diameter than the lower bore, where the base ring is adapted to be recessed in the upper bore with a top surface mounted flush with an outer surface of the skull surrounding the counterbore opening, and where the top surface is adapted to not overlap the outer surface of the skull when mounted within the counterbore opening;
    a lead securing element that mounts within an inner opening of the base ring, the lead securing element comprising two opposing semi-circular shaped members pivotally connected to one another; and
    a top cover that mounts to the base ring.

2. The DBS cap of claim 1, wherein the base ring is a continuous circular ring.

3. The DBS cap of claim 2, wherein the base ring is devoid of any tabs or wings that extend outward from its outer periphery.

4. The DBS cap of claim 1, wherein the inner opening extends from the top surface of the base ring to a bottom surface of the base ring.

5. The DBS cap of claim 4, wherein a distance between the top surface and the bottom surface is about 2 to 6 mm.

6. The DBS cap of claim 1, wherein the base ring includes at least one mounting hole that is adapted to receive a fastener that secures the base ring to a step at the interface between the upper and lower bores.

7. The DBS cap of claim 1, wherein the inner opening of the base ring includes a lower depression adapted to receive the lead securing element and a concentric upper depression adapted to receive the top cover.

8. The DBS cap of claim 7, further comprising an adhesive, the lead securing element being secured in place within the lower depression of the base ring via the adhesive.

9. The DBS cap of claim 8, wherein the top cover is secured in place within the upper depression of the base ring via the adhesive.

10. The DBS cap of claim 8, wherein the adhesive is a moisture-curable adhesive, an air-curable adhesive, or a light-curable adhesive.

11. The DBS cap of claim 1, wherein the two opposing semi-circular shaped members of the lead securing element are adapted to overlap to clamp onto the DBS lead.

12. The DBS cap of claim 11, wherein an inner edge of a first semi-circular shaped member of the two opposing semi-circular shaped members includes indentations that are adapted to receive the DBS lead.

13. The DBS cap of claim 12, wherein the indentions are curved.

14. The DBS cap of claim 13, wherein a radius of curvature of individual indentions is within a range of approximately 0.5 to 2 millimeters (mm).

15. The DBS cap of claim 12, wherein an inner edge of a second semi-circular-shaped member of the two opposing semi-circular shaped members is devoid of indentions.

16. The DBS cap of claim 11, wherein an inner edge of at least one of the two opposing semi-circular shaped members is pretreated with an adhesive that secures the DBS lead in place within the lead securing element when the two opposing semi-circular shaped members are overlapped.

17. The DBS cap of claim 16, wherein the adhesive is a moisture-curable adhesive, an air-curable adhesive, or a light-curable adhesive.

18. The DBS cap of claim 1, wherein the top cover comprises a notch provided within its periphery that is adapted to receive the DBS lead and enable it to pass through the DBS cap.

19. The DBS cap of claim 1, wherein the lead securing element is adapted to clamp the DBS lead via respective inner edges of the opposing semi-circular shaped members.

20. The DBS cap of claim 1, wherein the lead securing element is generally circular.

21. The DBS cap of claim 1, wherein an outer diameter of the base ring is approximately 20 to 30 mm.

22. The DBS cap of claim 1, wherein a diameter of the inner opening is approximately 12 to 16 mm.

\* \* \* \* \*